(12) United States Patent
Tornier

(10) Patent No.: US 6,582,469 B1
(45) Date of Patent: Jun. 24, 2003

(54) KNEE PROSTHESIS

(75) Inventor: Alain Tornier, Saint-Ismier (FR)

(73) Assignee: Tornier S.A., Saint-Ismier (FR)

( * ) Notice: Subject to any disclaimer, the term of this patent is extended or adjusted under 35 U.S.C. 154(b) by 0 days.

(21) Appl. No.: 09/555,530

(22) PCT Filed: Dec. 11, 1998

(86) PCT No.: PCT/FR98/02706

§ 371 (c)(1),
(2), (4) Date: Jun. 9, 2000

(87) PCT Pub. No.: WO99/30650

PCT Pub. Date: Jun. 24, 1999

(30) Foreign Application Priority Data

Dec. 12, 1997 (FR) .............................................. 97 16044

(51) Int. Cl.7 .................................................. A61F 2/38
(52) U.S. Cl. .................................. 623/20.27; 623/20.24
(58) Field of Search ........................... 623/20.14, 20.15, 623/20.21, 20.24, 20.25, 20.27, 20.28, 20.3, 20.31, 20.32, 20.33, 20.34, 20.35, 20.36

(56) References Cited

U.S. PATENT DOCUMENTS 5,358,527 A    10/1994    Forte 5,658,342 A    8/1997    Draganich et al.

FOREIGN PATENT DOCUMENTS

| EP | 0294298 | 12/1988 |
| EP | 0346183 | 12/1989 |
| GB | 2067412 | 7/1981 |

*Primary Examiner*—David J. Isabella
(74) *Attorney, Agent, or Firm*—Greenblum & Bernstein, P.L.C.

(57) ABSTRACT

Total prosthesis of a knee including a femoral element fitted with two condyles, a first of the condyles being external, a second of the condyles being internal, and a tibial plateau fitted with custom-made recesses to hold the condyles, wherein at least one of the condyles is integral on one of its sides with a convex cam ensuring posterior stability of the prosthesis. The tibial plateau has at least one track placed in the immediate vicinity of the recess holding the condyle integral with the cam, the at least one track being circumscribed by at least one curved abutment and at least one horizontal recess between posterior and anterior extremities of the tibial plateau. Provision is made between the condyles of the femoral element and the recesses of the tibial plateau for a free space and a notch for passage of a posterior cruciate ligament of a knee.

20 Claims, 7 Drawing Sheets

KNEE PROSTHESIS

BACKGROUND OF THE INVENTION

1. Field of the Invention

The present invention pertains to the field of improvements in total knee prostheses which comprise, as is customary, a femoral element and a tibial plateau. The femoral element is used to replace the destroyed condyles of the femur, while the tibial plateau replaces the defective upper part of the tibia.

2. Discussion of Background Information

Prostheses of this type are already available. They are essentially sliding prostheses, with or without preservation of the posterior cruciate ligament, and in which the femoral element moves over a small surface area in relation to the tibial plateau.

Document GB-A-2 067 412 describes a knee prosthesis in which the femoral element is fitted between its two condyles with a passage which terminates in a convex cam. The tibial plateau of the present prosthesis has recesses to hold the condyles and a concave ramp rising up toward the femoral element and stretching widely between both its condyles.

When the cam is engaged with the ramp, and the free angle is shifted, a very tight fit is created because of the large lever arm formed by attachment of the tibial plateau to the upper part of the tibia.

Moreover, the broad elongation of the ramp of the tibial plateau considerably restricts the amplitude of tibial rotation in relation to the femur.

Finally, the height of the ramp of the tibial plateau requires considerable resection of the femoral epiphysis, which clearly leads to a considerable reduction of its resistance.

These drawbacks have been overcome in Applicant's European patent No. 0 294 298. The total knee prosthesis described in this document includes a femoral element fitted with two asymmetrical condyles and a convex cam which is placed between the two condyles and fashioned as a third condyle.

The tibial plateau consists of a horizontal track which holds the convex cam of the femoral element which is situated below the level of the recesses on which the condyles of the femoral element move. Between the recesses, and aligned with the track, the tibial plateau includes a concave ramp which has the shape of a curved abutment holding the cam at a slight distance from the tibial plateau for the entire length of the course in which both elements are in contact: this reduces as much as possible any forces working on the tibial plateau.

Because of the low-lying position of the cam or third condyle, the lever arm created by its action on the ramp or tibial plateau abutment is reduced as much as possible, so that any forces transmitted to the tibia are minimal.

Total prostheses of the knee as described above have certain drawbacks: it is impossible to retain the posterior cruciate ligament because of the central placement of the convex cam between the two condyles.

The femur of a healthy knee is composed of two distal/posterior condyles which are separated by a space allowing passage of the posterior cruciate ligament which stabilizes the joint in the posterior position.

Improvements made to the knee prosthesis in accordance with the present invention aim to preserve passage of the posterior cruciate ligament while retaining the advantages of the convex cam as described in European patent No. 0 294 298.

SUMMARY OF THE INVENTION

The total prosthesis of the knee according to the present invention comprises a femoral element fitted with two condyles, one external, the other internal, at least one of which is integral on one of its sides with a convex cam ensuring posterior stability. A tibial plateau comprises two custom-made recesses to hold the condyles and at least one track placed in the immediate vicinity of the recess holding the condyle integral with the convex cam. The track is circumscribed by at least one curved abutment and at least one horizontal recess 19, 24 between the plateau provison posterior and anterior extremities of the tibial is made between the two condyles of the femoral element and the two recesses of the tibial plateau for a free space and a notch for the passage of the posterior cruciate ligament of the knee, respectively.

The total prosthesis of the knee according to the present invention has, on the internal side of one condyle of the femoral element, a convex cam fashioned as a third condyle in a manner limiting the dimensions of the free space communicating with the notch of the tibial plateau through which the posterior cruciate ligament of the knee passes, while the convex cam works with a track situated between and below the level of the recesses holding the said condyles.

The total prosthesis of the knee has, on the external side of one condyle of the femoral element, a convex cam fashioned as a third condyle in a manner limiting the free space between the external and internal condyles communicating with the notch of the tibial plateau through which the posterior cruciate ligament of the knee passes, while the convex cam works with a track situated on the outside and below the level of the recess holding the condyle.

The total prosthesis of the knee according to the present invention has, on the internal sides of each condyle of the femoral element, a convex cam fashioned as a third condyle in a manner limiting between the cams installed on opposite sides of it, the dimensions of the free space communicating with the notch of the tibial plateau through which the posterior cruciate ligament of the knee passes, while each convex cam works with a track situated between and below the level of the recesses holding the condyles.

The total prosthesis of the knee according to the present invention has a tibial plateau fitted with at least one track holding the convex cam connected to the femoral element and which includes at the side of the posterior extremity of the plateau a horizontal recess situated below the level of the custom-made recesses holding the condyle, the recess extending toward the anterior extremity of the plateau via a curved abutment which is raised against the tibia.

The total prosthesis of the knee according to the present invention has a tibial plateau fitted with at least one track holding the convex cam connected to the femoral element and which includes, at the side of the posterior extremity of the plateau, a first curved abutment rising slightly above the custom-made recesses holding the condyles, the first abutment extending toward the anterior extremity of the plateau via a second curved abutment which is raised against the tibia.

The total prosthesis of the knee according to the present invention has a tibial plateau fitted with at least one track holding the convex cam connected to the femoral element and which includes, at the side of the posterior extremity of the plateau, a curved abutment rising slightly above the recesses provided for holding the condyles, the abutment extending toward the anterior extremity of the plateau via a horizontal recess situated below the level of the recesses.

The total prosthesis of the knee according the present invention has a cam with a curved shape extending from the camber to the anterior wing of the femoral element.

The total prosthesis of the knee according to the present invention has a cam, a portion of which is torus shaped.

The total prosthesis of the knee according to the present invention has a cam which is less wide than the planned width of the external and internal condyles.

According to the invention, total prosthesis of a knee comprises a femoral element fitted with two condyles, a first of the condyles being external, a second of the condyles being internal, and a tibial plateau fitted with custom-made recesses to hold the condyles, wherein at least one of the condyles is integral on one of its sides with a convex cam ensuring posterior stability of the prosthesis, the tibial plateau having at least one track placed in the immediate vicinity of the recess holding the condyle integral with the cam. The at least one track is circumscribed by at least one curved abutment and at least one horizontal recess between posterior and anterior extremities of the tibial plateau, provision being made between the condyles of the femoral element and the recesses of the tibial plateau for a free space and a notch for passage of a posterior cruciate ligament of a knee.

According to another aspect of the invention, an internal side of one of the two condyles of the femoral element is integral with the convex cam designed as a third condyle in a manner to limit the dimensions of the free space communicating with the notch of the tibial plateau through which the posterior cruciate ligament of a knee passes, while the convex cam cooperates with the track located between and below the level of the recesses holding the two condyles.

Further, the tibial plateau is fitted with the at least one track holding the convex cam connected to the femoral element and which includes at the side of the posterior extremity of the plateau a horizontal recess located below the level of the custom-made recesses holding the condyles, the horizontal recess extending toward the anterior extremity of the plateau via a curved abutment which is raised against the tibia.

Alternatively, the tibial plateau is fitted with the at least one track holding the convex cam connected to the femoral element and which includes at the side of the posterior extremity of the plateau a first curve abutment rising slightly above the custom-made recesses holding the condyles, the first abutment extending toward the anterior extremity of the plateau via a second curved abutment which is raised against a tibia.

According to yet another alternative, the tibial plateau is fitted with the at least one track holding the convex cam connected to the femoral element and which includes at a side of the posterior extremity of the plateau a curved abutment rising slightly above the custom-made recesses holding the condyles, the abutment extending toward the anterior extremity of the plateau via a horizontal recess situated below the level of the recesses.

According to another aspect of the invention, an external side of one of the two condyles of the femoral element is integral with the convex cam fashioned as a third condyle in a manner to limit the free space between the two condyles communicating with the notch of the tibial plateau through which the posterior cruciate ligament of a knee passes, while the convex cam cooperates with the track located on the outside and below the level of the recess holding the condyle.

According to yet another aspect of the invention, the two condyles have internal sides, the first and the second condyle being integral on the internal sides thereof with a respective convex cam, the convex cams being designed as a third condyle in a manner to limit, between the cams installed on opposite sides, the dimensions of the free space communicating with the notch of the tibial plateau through which the posterior cruciate ligament of a knee passes, the at least one track comprising a separate track for each convex cam, each convex cam cooperating with its respective track located between and below the level of the recesses holding the condyles.

The tibial plateau is fitted with the at least one track holding the convex cam connected to the femoral element and which includes at the side of the posterior extremity of the plateau a horizontal recess located below the level of the custom-made recesses holding the condyles, the horizontal recess extending toward the anterior extremity of the plateau via a curved abutment which is raised against a tibia.

The side of the posterior extremity of the plateau may alternatively include a first curve abutment rising slightly above the custom-made recesses holding the condyles, the first abutment extending toward the anterior extremity of the plateau via a second curved abutment which is raised against a tibia.

As a further alternative, the side of the posterior extremity of the plateau may include a curved abutment rising slightly above the custom-made recesses holding the condyles, the abutment extending toward the anterior extremity of the plateau via a horizontal recess situated below the level of the recesses.

According to another aspect of the invention, the cam has a curved shape extending from a camber to an anterior wing of the femoral element. Further, a portion of the cam may be torus-shaped. The cam may have a torus surface. Further yet, the cam is narrower than the width of the two condyles.

The figures of the drawings, description which follows relates to the description of which is non-limiting and for illustrative purposes only, to permit better understanding of the invention, and its special features and likely advantages:

DETAILED DESCRIPTION OF THE PRESENT INVENTION

Figure 1:
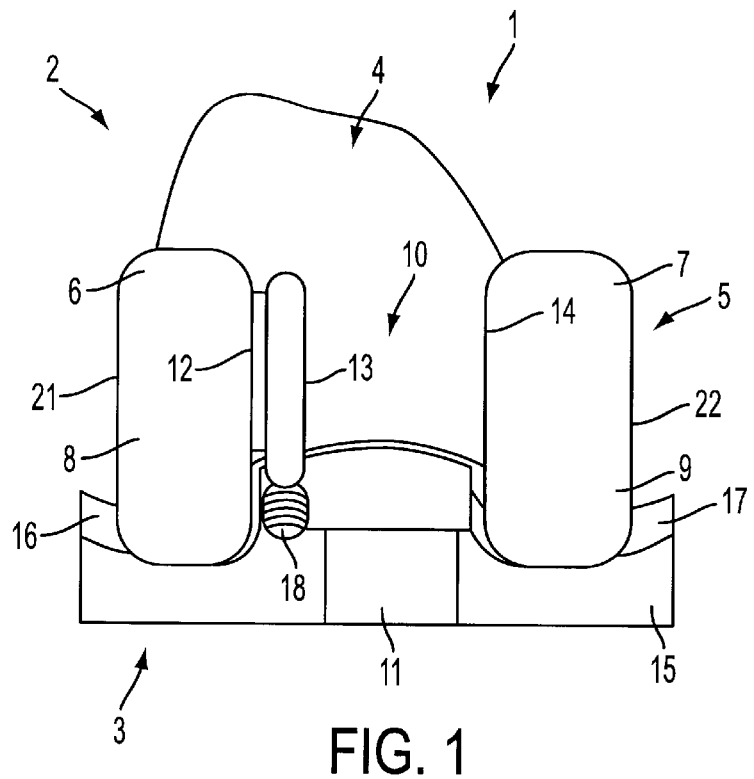
FIG. 1 is a view illustrating the total prosthesis of the knee according to the present invention.

FIG. 1 displays a total prosthesis of the knee 1 which essentially comprises a femoral element 2 and a tibial plateau 3.

In transverse section, the femoral element 2 is U-shaped overall i.e. it is formed from an initial anterior wing 4 which extends by way of a second posterior wing 5.

The flat internal surfaces of both these wings are intended to come together with the flattened ends of the femoral epiphysis (not shown) produced by sectioning the epiphysis anteriorly and posteriorly.

The posterior wing 5 comprises of two distinct and parallel cambers 6 and 7 integral with the anterior camber 4. The external surface of cambers 6 and 7 and the anterior wing 4 have a curved shape defining the limits of two lateral condyles 8 and 9 which may be symmetrical or asymmetrical depending on the usage of the prosthesis 1.

The external condyle 8 is separated from the internal condyle 9 by a free space 10 which is in communication with a space or notch 11 made in the posterior part of the tibial plateau 3 to allow passage of the posterior cruciate ligament (not shown).

On its internal side 12 and in the free space 10 the external condyle 8 contains a convex cam 13 forming a third condyle. The cam 13 has a curved shape which extends from the camber 6 to the anterior wing 4.

The convex cam 13 integral with the external condyle 8 defines, together with the opposing and internal side 14 of the internal condyle 9, the dimensions of the free space 10 provided for the passage of the cruciate ligament.

The tibial plateau 3 is made of a plastic material element 15 with a very low coefficient of friction designed to be fitted on a metallic plate fused to a stem (not shown) for anchoring in the tibia.

Element 15 has grooves on either side of the notch 11 to form two recesses 16 and 17. The recesses hold condyles 8 and 9 respectively of the femoral element 2, thereby allowing rotatory movement of the artificial knee 1.

A track 18 is fitted between the two recesses 16 and 17, close to recess 16, which is intended to hold the convex cam 13 integral with the external condyle 8.

Figure 4:
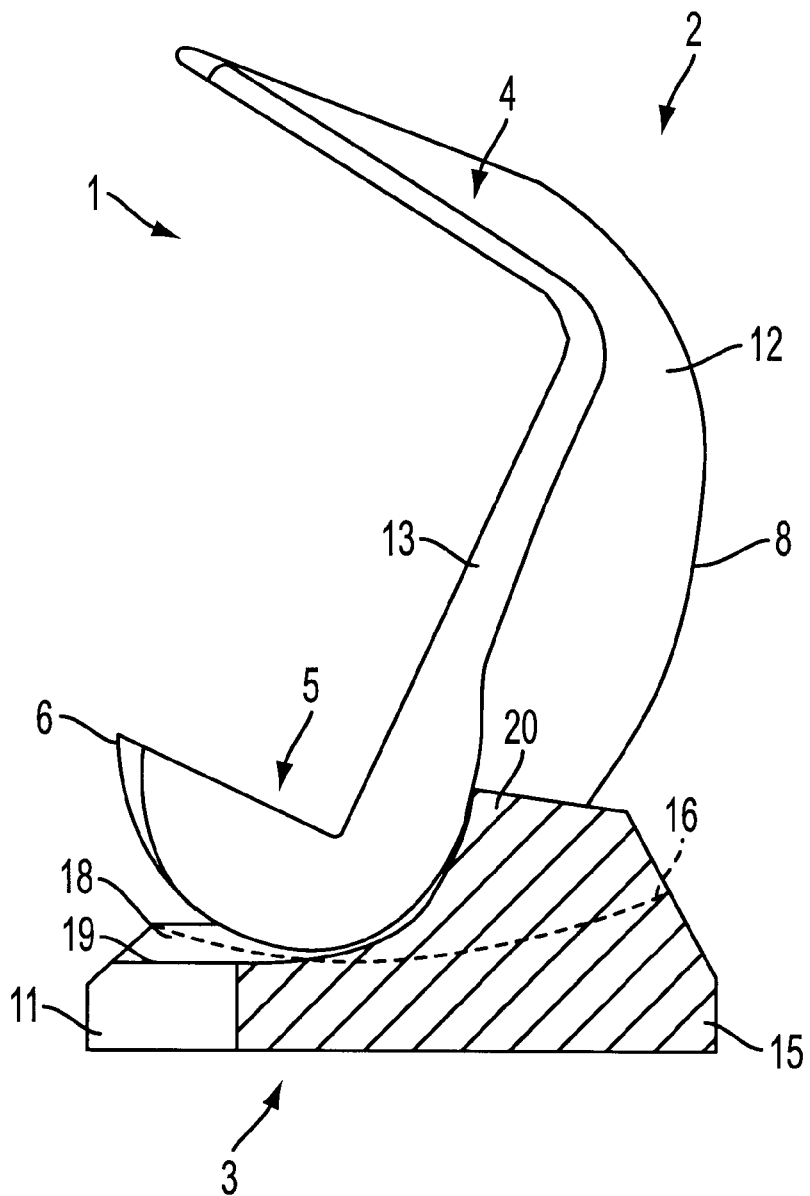
FIG. 4 is a view representing the manner in which the femoral element moves over the tibial plateau of the total prosthesis of the knee in accordance with the present invention.
Figure 5:
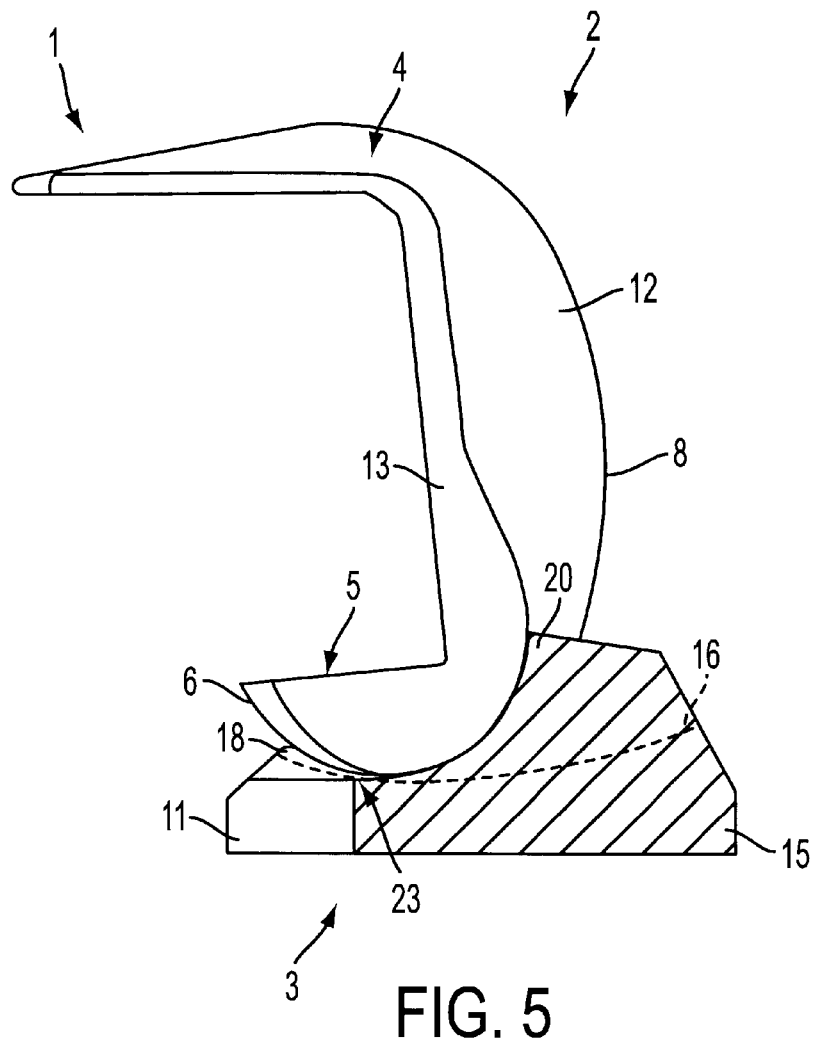
FIGS. 5 and 6 are views illustrating variants of the tibial plateau for movement of the femoral element of the total prosthesis of the knee according to the present invention.
Figure 6:
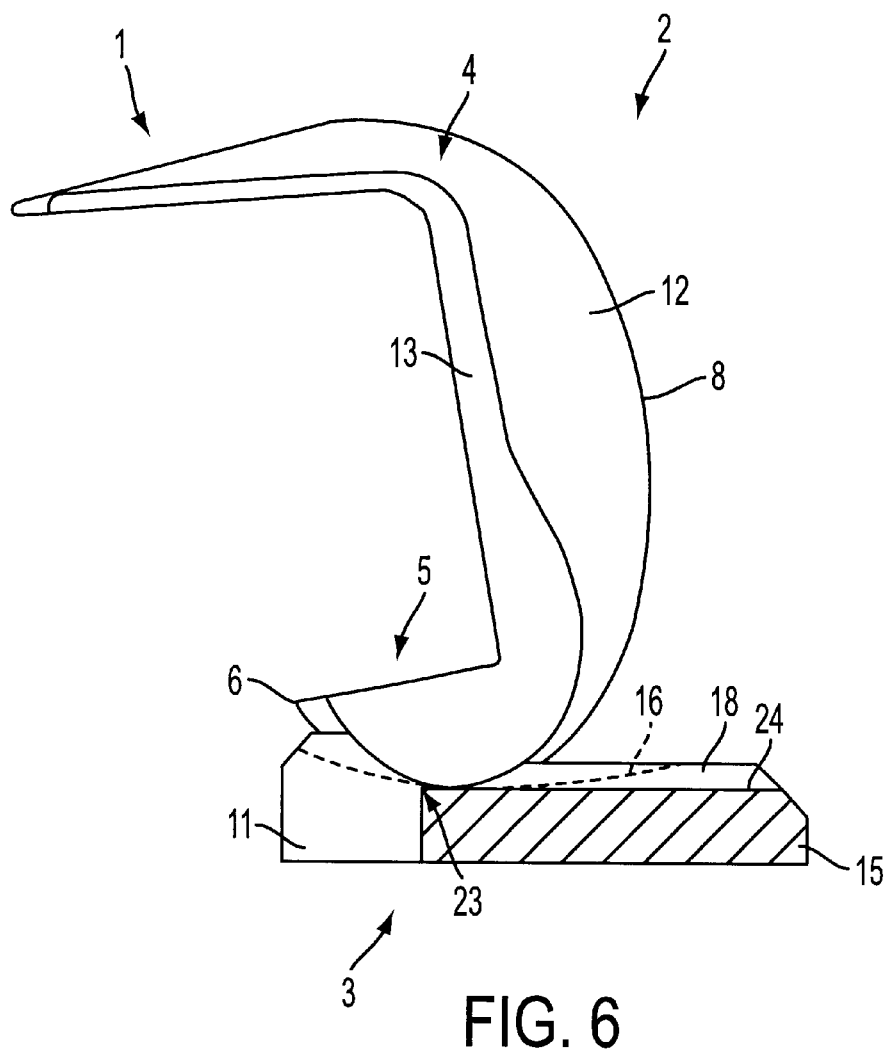

The shape of track 18 may vary in relation to the usage of the total prosthesis of the knee 1, as is shown in FIGS. 4 to 6.

Similarly to external condyle 8, the internal condyle 9 may be integral on its internal side 14 with a cam 13 working with a track 18 fitted between the two recesses 16 and 17, close to recess 17.

The convex cam 13, integral with the internal side 12 of the condyle 8 enhances anatomical movement of the prosthesis 1, since the external condyle 8 moves back further than the other in relation to the tibial plateau 3.

Figure 2:
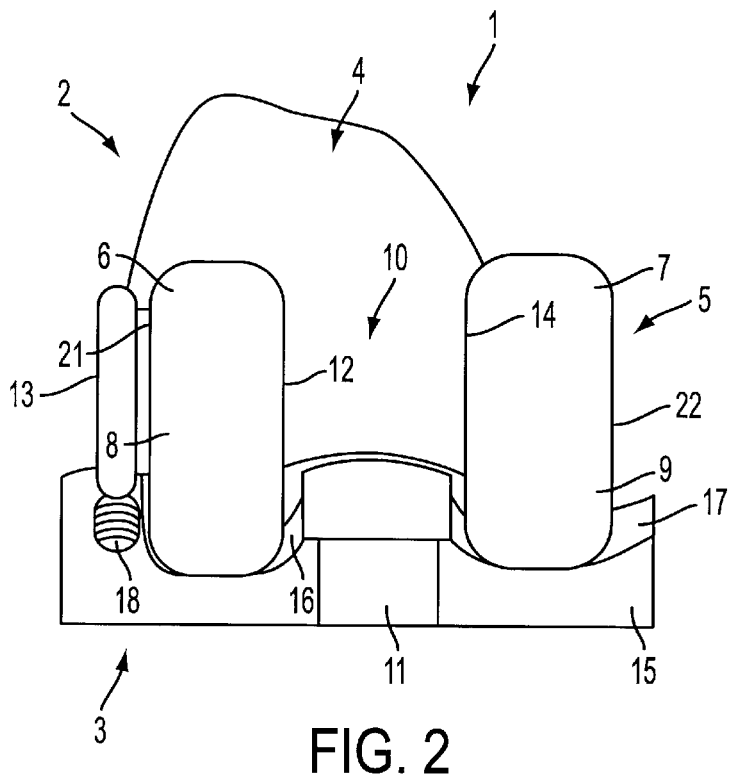
FIGS. 2 and 3 are views showing variants of the prosthesis of the knee according to the present invention.

FIG. 2 illustrates the external condyle 8 of the femoral element 2 which is integral with the convex cam 13 on its external side 21, while the tibial plateau 3 has a track 18 situated on the exterior of recess 16. In this embodiment the space 10 is bordered by the two condyles 8 and 9 of the femoral element 2 and serves as the passage for the posterior cruciate ligament.

In the same manner as the external condyle 8, the internal condyle 9 may be integral on its external side 22 with a convex cam 13, while the tibial plateau 3 has a track 18 situated on the exterior of recess 17.

Figure 3:
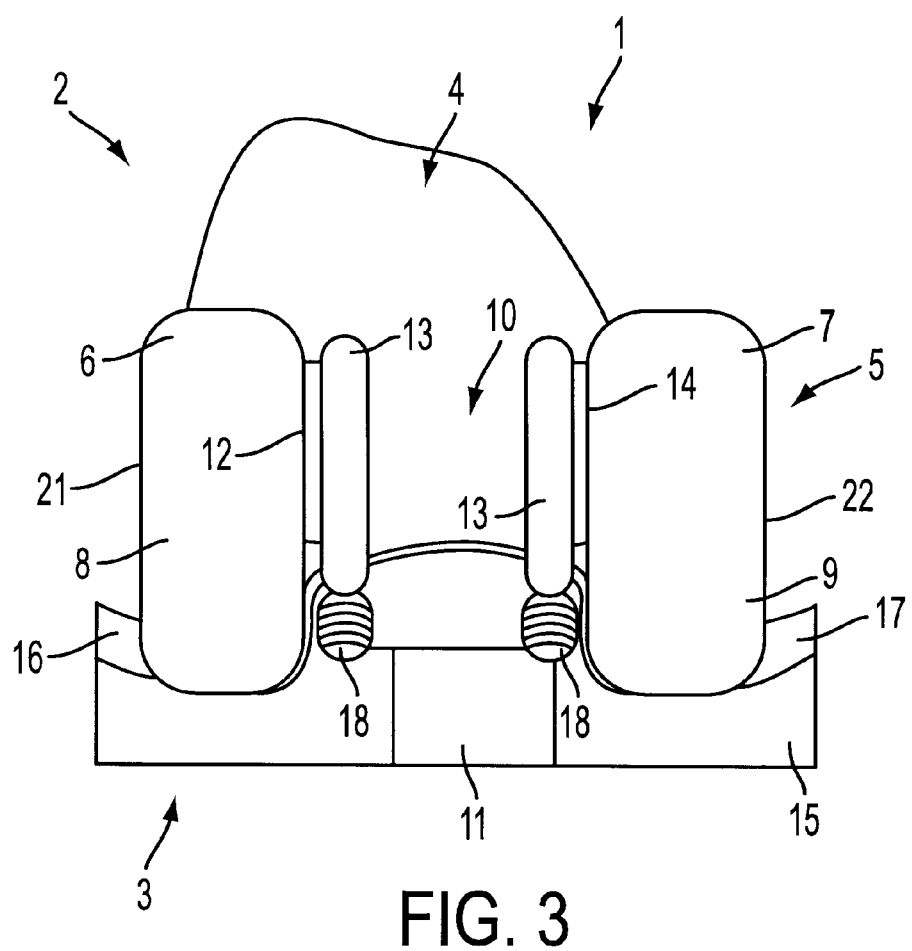

FIG. 3 illustrate another embodiment of the total prosthesis of the knee 1 in which the femoral element 2 has a convex cam 13 on the internal sides 12 and 14 of each condyle 8 and 9. Hence both opposed convex cams 13 define the dimensions of the free space 10 through which the posterior cruciate ligament passes. Each cam 13 of the femoral element 2 works together with a track 18 fitted between and close to the recesses 16 and 17 of the tibial plateau 3 custom-made to hold the condyles 8 and 9.

A portion of the convex cam 13 shown in FIGS. 1 to 3, and integral either with the external condyle 8 or the internal condyle 9, or both condyles 8 and 9, is torus-shaped to allow some side shift in rotation and avoid the "cut-off" phenomenon.

A torus-shaped portion designates a rotatory surface produced by a circle turning around an axis situated in its plane and not passing through its center.

The surface of the convex cam 13 is a torus surface.

Torus surface is a surface produced by a circle being displaced along any given line, the plane of the circle remaining perpendicular to the line of displacement.

When the femoral element 2 has a cam 13 on the internal sides 12 and 14 of each condyle 8 and 9 it will be noted that the usual weight-bearing structures of the knee is not changed (FIG. 3).

Furthermore, the femoral element 2 according to the invention, comprising one or two cams 13, allows side shift in rotation in relation to the tibial axis.

In addition, the femoral element 2 according to the invention, comprising one or two cams 13, circumvents the problem of patellar conflict common to knee prostheses of the anterior type.

It will be viewed that the convex cam 13, seen face on, is rounded and not very wide; its width is very much less than that provided for the external condyle 8 and internal condyle 9.

Depending on whether the posterior cruciate ligament is saved or not and the track 18 holding the convex cam 13 may take on different shapes.

Figure 7:
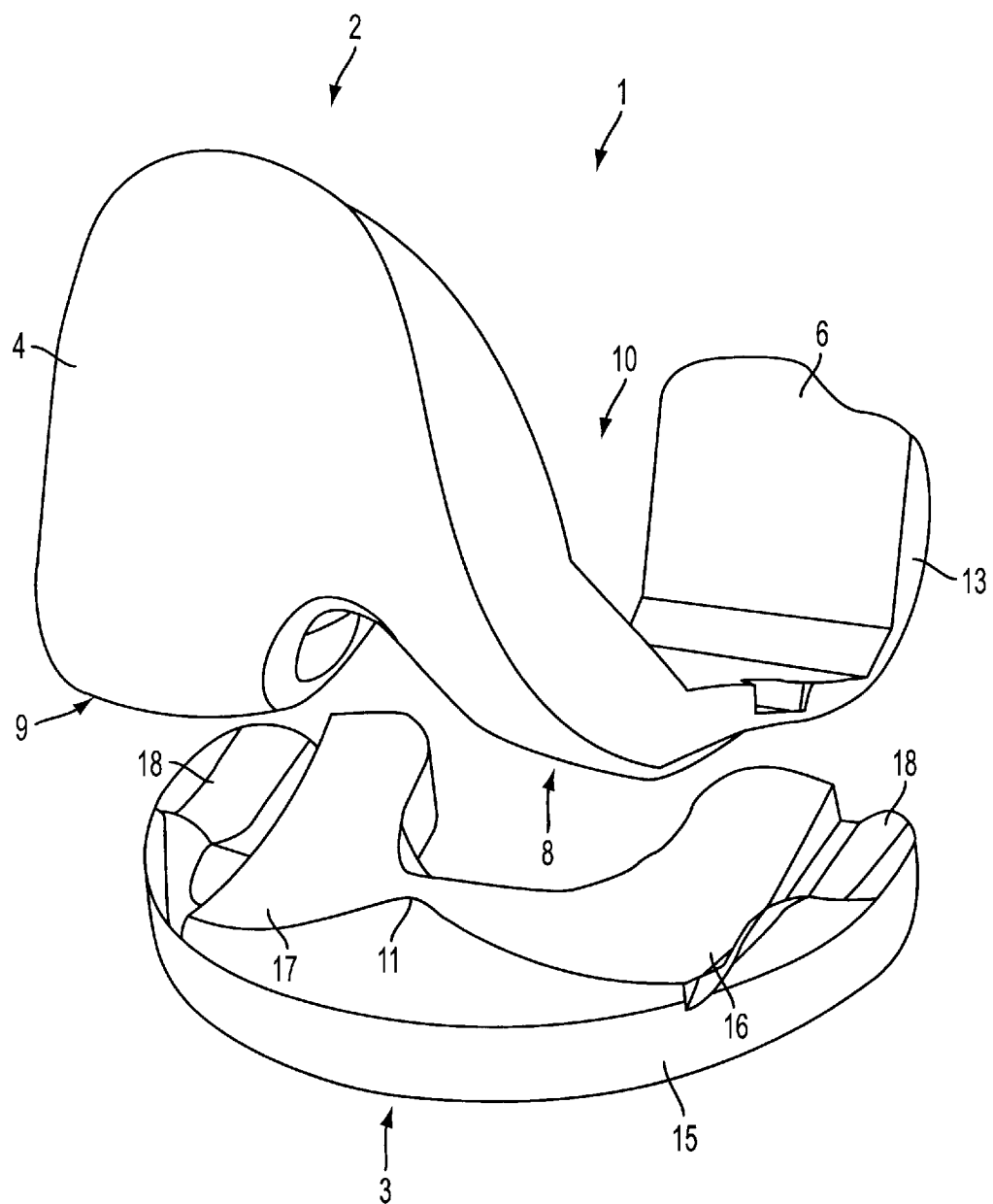
FIG. 7 and 8 illustrate perspective views of the prosthesis shown in FIG. 4.
Figure 8:
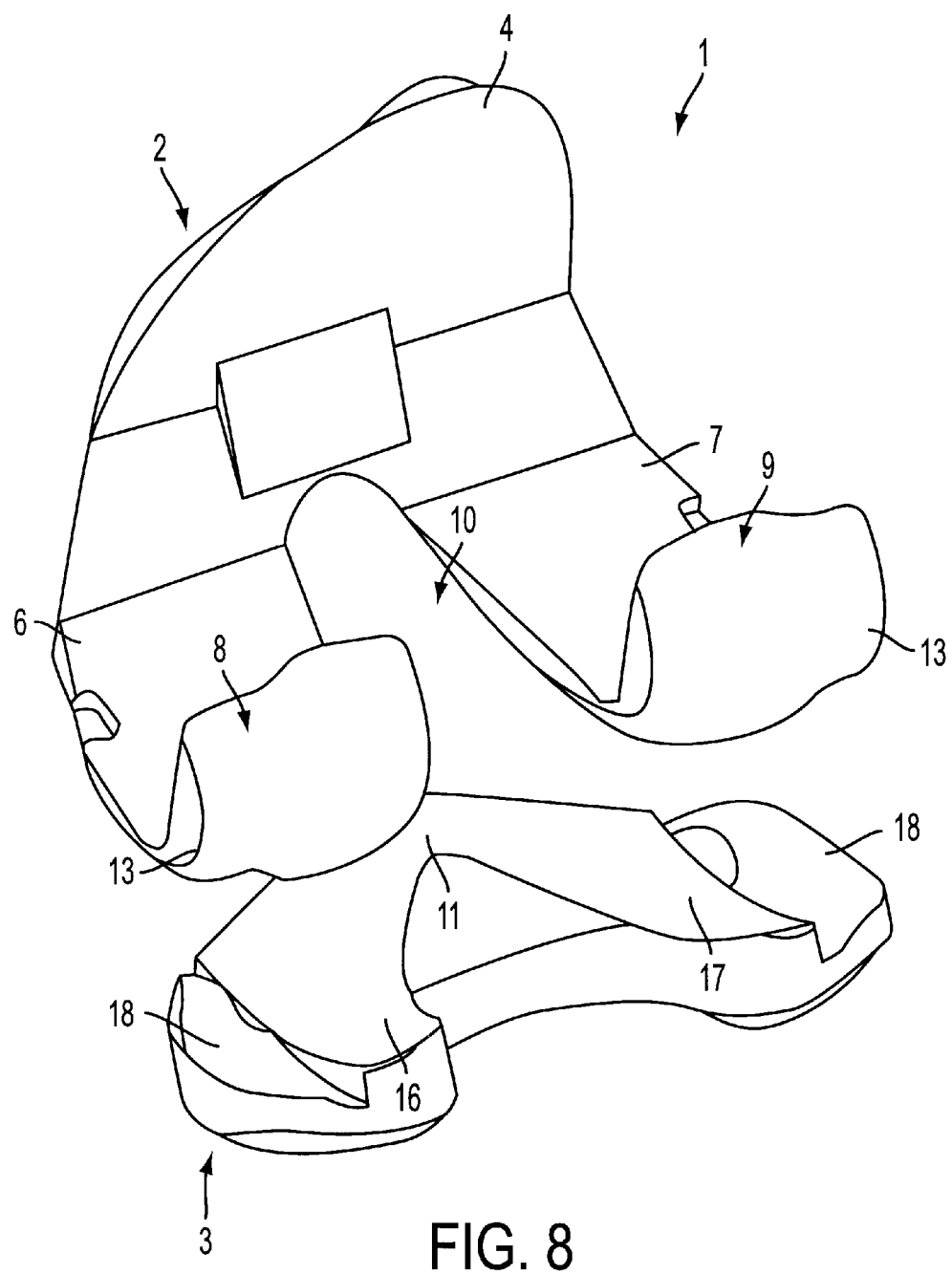

It can be seen from FIGS. 4, 7 and 8 that the track 18 includes, on the side of the posterior extremity of the plateau 3, a horizontal recess 19 which is extended toward the anterior extremity of the plateau by a curved abutment 20 raised against the tibia in the direction of the femoral element 2. The horizontal recess 19 is situated below the recesses 16 and 17 holding the condyles 8 and 9 of the femoral element 2 (FIG. 4).

Tibial plateau 3 may be used with a femoral element 2 as described in FIGS. 1 to 3 to form a total prosthesis of the knee 1 with or without preservation of the posterior cruciate ligament.

In FIG. 5 the track 18 includes, on the side of the posterior extremity of the tibial plateau 3, i.e. on the side of the notch 11, a first curved abutment 23 which is slightly raised above the recesses 16 and 17 provided to hold the condyles 8 and 9.

The first abutment 23 is extended toward the anterior extremity of the plateau by a second curved abutment 20 which is raised against the tibia.

The tibial plateau 3 in FIG. 5 may be used with a femoral element 2 as described in FIGS. 1 to 3 to allow preservation of the posterior cruciate ligaments, returning automatically to default mode, i.e. stabilized posterior functioning, should the ligament be destroyed subsequently.

In FIG. 6 the track 18 includes, on the side of the posterior extremity of the tibial plateau 3, i.e. at the level of the notch 11, the curved abutment 23 slightly raised above the recesses 16 and 17, and extended toward anterior extremity of the plateau by a horizontal recess 24 situated below the recesses 16 and 17 for the condyles 8 and 9 of the femoral element 2.

This tibial plateau 3 may thus be used with a femoral element 2 as described previously in relation to FIGS. 1 to 3 to form a total prosthesis of the knee 1 with preservation of the posterior cruciate ligament where backward movement is halted by the abutment 23 on displacement of the femoral element.

It should be noted moreover that the preceding description has been provided solely for illustration and that it does not limit the scope of the invention which continues to apply even if any production details described are replaced by an equivalent.

What is claimed is:

1. Total prosthesis of a knee comprising a femoral element having an external and an internal condyle, a tibial plateau formed with recesses configured for engagement with said condyles, wherein at least one convex cam is integral with at least one of said condyles, for ensuring posterior stability of the prosthesis, the tibial plateau having at least one complementary track formed therein adjacent one of said recesses engaging the condyle with the integral cam; said track being circumscribed by at least one curved abutment and at least one horizontal recess extending between posterior and anterior peripheries of the tibial plateau, the tibial plateau defining a free space and a notch to allow for passage of a posterior cruciate ligament of a knee.

2. Total prosthesis according to claim 1, wherein an internal side of one of the condyles of the femoral element is integral with said convex cam designed as a third condyle in a manner to limit the dimensions of the free space communicating with the notch of the tibial plateau through which the posterior cruciate ligament of the knee passes, while the convex cam cooperates with said track located between and below the level of the recesses holding the condyles.

3. Total prosthesis according to claim 2, wherein the tibial plateau is fitted with said at least one track holding the convex cam connected to the femoral element, said track extending in an anterior-posterior direction and being located below the level of the recesses configured for engagement with said condyles, and being formed by a horizontal recess that extends upwardly on a curved abutment located on the anterior part of said plateau.

4. Total prosthesis according to claim 2, wherein the tibial plateau is fitted with said at least one track holding the convex cam connected to the femoral element and which includes at the side of the posterior extremity of said plateau a first curved abutment rising slightly above the recesses configured for engagement with said condyles, said first curved abutment extending toward the anterior extremity of said plateau and a second curved abutment which is curved upwardly.

5. Total prosthesis according to claim 2, wherein the tibial plateau is fitted with said at least one track holding the convex cam connected to the femoral element and which includes at the side of the posterior extremity of said plateau a curved abutment rising slightly above the recesses configured for engagement with said condyles, said abutment extending toward the anterior extremity of said plateau and including a horizontal recess situated below the level of said recesses configured for engagement with said condyles.

6. Total prosthesis according to claim 1, wherein an external side of one of the condyles of the femoral element is integral with said convex cam designed as a third condyle in a manner to limit the free space between the condyles communicating with the notch of the tibial plateau through which the posterior cruciate ligament of the knee passes, while the convex cam cooperates with said track located on the outside and below the level of the recess holding one of the condyles.

7. Total prosthesis according to claim 6, wherein the tibial plateau is fitted with said at least one track holding the convex cam connected to the femoral element, said track extending in an anterior-posterior direction and being located below the level of the recesses configured for engagement with said condyles, and being formed by a horizontal recess that extends upwardly on a curved abutment located on the anterior part of said plateau.

8. Total prosthesis according to claim 6, wherein the tibial plateau is fitted with said at least one track holding the convex cam connected to the femoral element and which includes at the side of the posterior extremity of said plateau a first curved abutment rising slightly above the recesses configured for engagement with said condyles, said first curved abutment extending toward the anterior extremity of said plateau and a second curved abutment which is raised against a tibia.

9. Total prosthesis according to claim 6, wherein the tibial plateau is fitted with said at least one track holding the convex cam connected to the femoral element and which includes at the side of the posterior extremity of said plateau a curved abutment rising slightly above the recesses configured for engagement with said condyles, said abutment extending toward the anterior extremity of said plateau and including a horizontal recess situated below the level of said recesses configured for engagement with said condyles.

10. Total prosthesis according to claim 1, wherein the condyles have internal sides, said condyles being integral on the internal sides thereof with a respective convex cam, said convex cams being designed as a third condyle in a manner to limit, between the cams installed on opposite sides, the dimensions of the free space communicating with the notch of the tibial plateau through which the posterior cruciate ligament of the knee passes, said at least one track comprising a separate track for each convex cam, each convex cam cooperating with its respective track located between and below the level of the recesses configured for engagement with said condyles.

11. Total prosthesis according to claim 1, wherein the tibial plateau is fitted with said at least one track holding the convex cam connected to the femoral element and which includes at the side of the posterior extremity of said plateau a horizontal recess located below the level of the recesses configured for engagement with said condyles, said horizontal recess extending toward the anterior extremity of said plateau via a curved recess formed on an abutment, said abutment being curved upwardly.

12. Total prosthesis according to claim 1, wherein the tibial plateau is fitted with said at least one track holding the convex cam connected to the femoral element and which includes at the side of the posterior extremity of said plateau a first curved abutment rising slightly above the recesses configured for engagement with said condyles, said first curved abutment extending toward the anterior extremity of said plateau and a second curved abutment which is curved upwardly.

13. Total prosthesis according to claim 10, wherein the tibial plateau is fitted with said at least one track holding the convex cam connected to the femoral element and which includes at the side of the posterior extremity of said plateau a curved abutment rising slightly above the recesses configured for engagement with said condyles, said curved abutment extending toward the anterior extremity of said plateau and a horizontal recess situated below the level of said recesses configured for engagement with said condyles.

14. Total prosthesis according to claim 10, wherein the tibial plateau is fitted with said at least one track holding the convex cam connected to the femoral element and which includes at the side of the posterior extremity of said plateau a horizontal recess located below the level of the recesses configured for engagement with said condyles, said horizontal recess extending toward the anterior extremity of said plateau via a curved recess formed on an abutment, said abutment being curved upwardly.

15. Total prosthesis according to claim 1, wherein the tibial plateau is fitted with said at least one track holding the convex cam connected to the femoral element and which includes at the side of the posterior extremity of said plateau a first curved abutment rising slightly above the recesses configured for engagement with said condyles, said first curved abutment extending toward the anterior extremity of said plateau and a second curved abutment which is curved upwardly.

16. Total prosthesis according to claim 1, wherein the tibial plateau is fitted with said at least one track holding the convex cam connected to the femoral element and which includes at the side of the posterior extremity of said plateau a curved abutment rising slightly above the recesses configured for engagement with said condyles, said curved abutment extending toward the anterior extremity of said plateau and a horizontal recess situated below the level of said recesses configured for engagement with said condyles.

17. Total prosthesis according to claim 1, wherein the cam has a curved shape extending from a camber to an anterior wing of the femoral element.

18. Total prosthesis according to claim 1, wherein a portion of the cam is torus-shaped.

19. Total prosthesis according to claim 1, wherein the cam has a torus surface.

20. Total prosthesis according to claim 1, wherein the cam is narrower than the width of the condyles.

* * * * *